(12) United States Patent
Chen et al.

(10) Patent No.: US 12,018,063 B2
(45) Date of Patent: Jun. 25, 2024

(54) PD-1-BASED VACCINES AGAINST CORONAVIRUS INFECTION

(71) Applicant: Versitech Limited, Hong Kong (CN)

(72) Inventors: Zhiwei Chen, Hong Kong (CN); Kwok Yung Yuen, Hong Kong (CN); Honglin Chen, Hong Kong (CN); Yik Chun Wong, Hong Kong (CN); Li Liu, Hong Kong (CN)

(73) Assignee: Versitech Limited, Hong Kong (CN)

( * ) Notice: Subject to any disclaimer, the term of this patent is extended or adjusted under 35 U.S.C. 154(b) by 537 days.

(21) Appl. No.: 17/186,822

(22) Filed: Feb. 26, 2021

(65) Prior Publication Data

US 2021/0261644 A1    Aug. 26, 2021

Related U.S. Application Data

(60) Provisional application No. 62/982,015, filed on Feb. 26, 2020.

(51) Int. Cl.
*C07K 14/705*    (2006.01)
*A61K 39/12*    (2006.01)
*A61P 31/14*    (2006.01)
*C07K 14/165*    (2006.01)

(52) U.S. Cl.
CPC ...... *C07K 14/70521* (2013.01); *C07K 14/165* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil |
| 5,916,588 | A | 6/1999 | Popescu |
| 6,090,406 | A | 7/2000 | Popescu |
| 6,207,646 | B1 | 3/2001 | Krieg |
| 6,239,116 | B1 | 5/2001 | Krieg |
| 6,299,884 | B1 | 10/2001 | Van Nest |
| 6,429,199 | B1 | 8/2002 | Krieg |
| 6,451,325 | B1 | 9/2002 | Van Nest |
| 9,029,315 | B2 | 5/2015 | Chen |
| 2012/0121634 | A1* | 5/2012 | Chen .............. A61P 31/14 604/20 |
| 2014/0302070 | A1* | 10/2014 | Chen .............. C07K 16/2818 435/375 |
| 2017/0202955 | A1 | 7/2017 | Podda |
| 2019/0351048 | A1* | 11/2019 | Rauch .............. C12N 15/86 |
| 2023/0097958 | A1* | 3/2023 | Chen .............. C07K 14/4748 424/277.1 |

FOREIGN PATENT DOCUMENTS

| | | |
|---|---|---|
| CN | 110732021 | 1/2020 |
| EP | 0626169 | 11/1994 |
| EP | 0735898 | 10/1996 |
| EP | 0761231 | 3/1997 |
| EP | 0835318 | 4/1998 |
| WO | 1990014837 | 12/1990 |
| WO | 1994000153 | 1/1994 |
| WO | 1995017211 | 6/1995 |
| WO | 1996011711 | 4/1996 |
| WO | 1996033739 | 10/1996 |
| WO | 1998040100 | 9/1998 |
| WO | 1998042375 | 10/1998 |
| WO | 1998057659 | 12/1998 |
| WO | 1999011241 | 3/1999 |
| WO | 1999027960 | 6/1999 |
| WO | 1999052549 | 10/1999 |
| WO | 1999062923 | 12/1999 |
| WO | 2000007621 | 2/2000 |
| WO | 2000023105 | 4/2000 |
| WO | 2001021152 | 3/2001 |
| WO | 2001021207 | 3/2001 |
| WO | 2001095935 | 12/2001 |
| WO | 2002026757 | 4/2002 |
| WO | 2003035836 | 5/2003 |
| WO | 2012062218 | 5/2012 |
| WO | 2019241758 | 12/2019 |

OTHER PUBLICATIONS

Yang, Z. Y. et al. A DNA vaccine induces SARS coronavirus neutralization and protective immunity in mice. Nature 428, 561-564 (2004).*
Liu, L. et al. Natural mutations in the receptor binding domain of spike glycoprotein determine the reactivity of cross-neutralization between palm civet coronavirus and severe acute respiratory syndrome coronavirus. J Virol 81, 4694-4700 (2007).*
NCBI YP_009724397.2 (Jan. 17, 2020); 2 pages.*
NCBI YP_009724390.1 (Jan. 5, 2020); 3 pages.*
Zhou et al. (2013) Potentiating functional antigen-specific CD8+ T cell immunity by a novel PD1 isoform-based fusion DNA vaccine. Mol. Ther. 21: 1445-1455.*

(Continued)

*Primary Examiner* — Ilia I Ouspenski
(74) *Attorney, Agent, or Firm* — PABST PATENT GROUP LLP

(57) ABSTRACT

Disclosed soluble PD-1 (sPD-1) proteins and nucleic acids, and therapeutic compositions comprising sPD-1 proteins and nucleic acids, for enhancing immunity of a subject against coronavirus infection. Disclosed are soluble PD-1 fusion proteins that include a soluble PD-1 protein fragment and an antigenic protein fragment, preferably where the antigenic protein fragment comprises a coronavirus protein fragment. In some forms, the coronavirus protein fragment is derived from a coronavirus receptor binding domain (RBD) or a coronavirus nucleoprotein (N). In some forms, the sPD-1 proteins, nucleic acids, and compositions are formulated as a vaccine composition. Also disclosed are methods for treating a subject at risk of or suffering a coronavirus infection.

14 Claims, 1 Drawing Sheet

Specification includes a Sequence Listing.

(56) References Cited

OTHER PUBLICATIONS

Sun et al., Cell, 182:734-743 (2020) (provided by Applicant).*
Zhou et al., Immunity 53:864-877 (2020) (provided by Applicant).*
McCray et al., J. Virol, 81:813-821 (2007) (provided by Applicant).*
Winkler et al., Nat Immunol 21:1327-1335 (2020) (provided by Applicant).*
Zhou et al., EBioMedicine, 75:103762 (2022) (provided by Applicant).*
Andrianov, et al., "Preparation of hydrogel microspheres by coacervation of aqueous polyphosphazene solutions", Biomaterials, 19(1-3): 109-115 (1998).
Barr, et al., "ISCOMs and other saponin based adjuvants", Advanced Drug Delivery Reviews, 32(3): 247-27 (1998).
Beignon, et al., "The LTR72 Mutant of Heat-Labile Enterotoxin of Escherichia coli Enhances the Ability of Peptide Antigens To Elicit CD4+ T Cells and Secrete Gamma Interferon after Coapplication onto Bare Skin", Infection and Immunity, 70: 3012-3019 (2002).
Bhagat, et al., "CpG penta-and hexadeoxyribonucleotides as potent immunomodulatory agents", BBRC, 300(4): 853-861 (2003).
Blackwell, et al., "CpG-A-induced monocyte IFN-gamma-inducible protein-10 production is regulated by plasmacytold dendritic cell-derived IFN-alpha", J. Immunol. 170: 4061-4068 (2003).
Johnson, et al., "Synthesis and biological evaluation of a new class of vaccine adjuvants: aminoalkyl glucosaminide 4-phosphates (AGPs)", Bioorg Med Chern Lett, 9(15): 2273-2278 (1999).
Kandimalla, et al., "Divergent synthetic nucleotide motif recognition pattern: design and development of potent immunomodulatory oligodeoxyribonucleotide agents with distinct cytokine induction profiles", Nucleic Acids Research, 31: 2393-2400 (2003a).
Kandimalla, et al., "Toll-like receptor 9: modulation of recognition and cytokine induction by novel synthetic CpG DNAs", Biochemical Society Transactions, 31 (part 3): 654-658 (2003b).
Kandimalla, et al., "Secondary structures in CpG oligonucleotides affect immunostimulatory activity", BBRC, 306(4): 948-95 (2003c).
Krieg, "CpG motifs: the active ingredient in bacterial extracts?", Nature Medicine, 9(7): 831-835 (2003).
Krieg, "From A to Z on CpG", TRENDS in Immunology, 23(2): 64-65 (2002).
McCluskie, et al., "Parenteral and mucosal prime-boost immunization strategies in mice with hepatitis B surface antigen and CpG DNA", FEMS Immunology and Medical Microbiology, 32(3):179-185 (2002).
Meraldi, et al., "OM-174, a new adjuvant with a potential for human use, induces a protective response when administered with the synthetic C-terminal fragment 242-310 from the circumsporozoite protein of Plasmodium berghei", Vaccine, 21(19-20): 2485-2491 (2003).
Pajak, et al., "The adjuvant OM-174 induces both the migration and maturation of murine dendritic cells in vivo", Vaccine, 21(9-10): 836-842 (2003).
Partidos, et al., "Heat-labile enterotoxin of Escherichia coli and its site-directed mutant LTK63 enhance the proliferative and cytotoxic T-cell responses to intranasally co-immunized synthetic peptides", Immunol. Lett., 67(3): 209-216 (1999).
Peppoloni, et al., "Mutants of the Escherichia coli heat-labile enterotoxin as safe and strong adjuvants for intranasal delivery of vaccines", Vaccines, 2(2): 285-293 (2003).
Pine, et al., "Intranasal immunization with influenza vaccine and a detoxified mutant of heat labile enterotoxin from Escherichia coli (LTK63)", J. Control Release, 85(1-3): 263-270 (2002).
Pizza, et al., "LTK63 and LTR72, two mucosal adjuvants ready for clinical trials", Int. J. Med. Microbiol., 290 (4-5): 455-461 (2003).
Pizza, et al., "Mucosal vaccines: nontoxic derivatives of LT and CT as mucosal adjuvants", Vaccine, 19(17-19): 2534-2541 (2001).
Podda, "The adjuvanted influenza vaccines with novel adjuvants: experience with the MF59-adjuvanted vaccine", Vaccine, 19(17-19): 2673-2680 (2001).
Ryan, et al., "Mutants of Escherichia coli heat-labile toxin act as effective mucosal adjuvants for nasal delivery of an acellular pertussis vaccine: differential effects of the nontoxic AB complex and enzyme activity on Th1 and Th2 cells", Infection and Immunity, 67(12): 6270-6280 (2003).
Scharton-Kersten, et al., "Transcutaneous Immunization with Bacterial ADP-Ribosylating Exotoxins, Subunits, and Unrelated Adjuvants", Infection and Immunity, 68(9): 5306-5313 (2000).
Singh, et al., "A novel bioadhesive intranasal delivery system for inactivated influenza vaccines", J. Cont. Rel., 70(3):267-276 (2001).
Sjolander, et al., "Uptake and adjuvant activity of orally delivered saponin and ISCOM vaccines", Advanced Drug Delivery Reviews, 34(2-3): 321-338 (1998).
Stanley, "Imiquimod and the imidazoquinolones: mechanism of action and therapeutic potential", Clin. Exp. Dermatol., 27(7): 571-577 (2002).
International Search Report for PCT/CN2021/072657 dated Apr. 22, 2021.

* cited by examiner

PD-1-BASED VACCINES AGAINST CORONAVIRUS INFECTION

CROSS-REFERENCE TO RELATED APPLICATIONS

This application is a claims priority to and benefit of U.S. Provisional Application No. 62/982,015, filed Feb. 26, 2020. Application No. 62/982,015, filed Feb. 26, 2020, is hereby incorporated herein by reference in its entirety.

REFERENCE TO SEQUENCE LISTING

The Sequence Listing submitted Mar. 16, 2021, as a text file named "UHK_00927_substitute_ST25.txt," created on Mar. 8, 2021, and having a size of 25,850 bytes is hereby incorporated by reference pursuant to 37 C.F.R. § 1.52(e)(5).

FIELD OF THE INVENTION

The present invention is generally in the field of vaccines against coronavirus infection, and in particular in the field of PD1-based vaccines against coronavirus infection.

BACKGROUND OF THE INVENTION

A novel coronavirus, designated as 2019 novel coronavirus (COVID-19; 2019 nCoV) by the World Health Organization (WHO), emerged in Wuhan, Henbei Province of China since December 2019. So far, there are more than 30 thousand laboratory confirmed infections, with about 2% of cases fatal. The 2019 nCoV has disseminated to other provinces of China and more than 20 countries mainly imported by humans traveling from the affected areas, Wuhan/Hubei. There are two possibilities of the subsequent prevalence: (1) 2019 nCoV will disappear from humans after a huge intervention measures currently implanted by China and many other countries; (2) 2019 nCoV may become a common cold virus and continue to circulate in humans, like other human coronavirus. Three coronaviruses have crossed species barriers and infected human since 2002/2003 of SARS coronavirus. It is reasonably to believe that other coronavirus from animal sources may emerge and infect humans in future. A rapid responsive and effective vaccine is needed for the current ongoing nCoV and future emerging coronavirus. Further, Humans do not have preexisting immunity to nCoV and there is a concern that this virus may cause a pandemic leading to significant mobility and mortality worldwide. A vaccine for prevention of infection by this nCoV is urgently needed.

Programmed death 1 (PD-1 or PD1), expressed primarily on T cells, is a receptor for B7-H1 molecule (also known as programmed death ligand 1 (PD-L1)) and B7-DC molecule (also known as programmed death ligand 2 (PD-L2)). PD-L1 is expressed on many different cell types, whereas PD-L2 is expressed only on antigen-presenting cells such as B cells, dendritic cells and macrophages.

The PD-1/PD-L pathway, which transmits negative signals to immune cells, plays a critical role in the modulation of immune responses during infection. The interaction of PD-1 with PD-L1/L2 inhibits T cell function during infection. Blockade of PD-1 during chronic infection by anti PD-1 antibody can result in enhanced B cell responses as well as rapid expansion and restoration of virus-specific polyfunctional CD8 T cells. Blockade of the PD-1/PD-L pathway also facilitates the restoration of humoral and cell-mediated immune responses during viral infection.

Novel strategies to develop an effective vaccine against the 2019 novel coronavirus (nCoV) with properties to provide broad cross protective activity are necessary.

It is an object of the present invention to provide vaccines against coronavirus infection.

It is also an object of the present invention to provide methods of generating vaccines against coronavirus infection.

It is a further object of the present invention to provide methods of eliciting an immune response against coronavirus in a mammal.

Any discussion of documents, acts, materials, devices, articles or the like that has been included in the present specification is not to be taken as an admission that any or all of these matters form part of the prior art base or were common general knowledge in the field relevant to the present disclosure as it existed before the priority date of each claim of this application.

SUMMARY OF THE INVENTION

Disclosed soluble PD-1 (sPD-1) proteins and nucleic acids, and therapeutic compositions comprising sPD-1 proteins and nucleic acids, for enhancing immunity of a subject against coronavirus infection. In some forms, the sPD-1 proteins, nucleic acids, and compositions are formulated as a vaccine composition.

In some forms, sPD-1 proteins are sPD-1 protein variants. In some forms, the sPD-1 protein variant is mspd1-14del, which has an amino acid sequence comprising SEQ ID NO:3. In some forms, the sPD-1 protein variant is mspd1-322 mu, which has an amino acid sequence comprising SEQ ID NO:5. In some forms, the sPD-1 protein variant is hspd1-14del, which was found in healthy Chinese people. The hspd1-14del variant has an amino acid sequence comprising SEQ ID NO:9.

Also disclosed are nucleic acid molecules that encode the sPD-1 proteins. In some forms, the nucleic acid molecule encodes mspd1-14del, and has a sequence comprising SEQ ID NO:4. In some forms, the nucleic acid molecule encodes mspd1-322mu, and has a sequence comprising SEQ ID NO:6. In some forms, the nucleic acid molecule encodes hspd1-14del, and has a sequence comprising SEQ ID NO:10.

Also disclosed are sPD-1 fusion proteins. In some forms, the sPD-1 fusion protein includes both an amino acid sequence selected from the group consisting of SEQ ID NO:1, SEQ ID NO:7, SEQ ID NO:3, SEQ ID NO:5, and SEQ ID NO:9 and an amino acid sequence selected from the group consisting of SEQ ID NO:11 or SEQ ID NO:12. Also disclosed are sPD-1 fusion nucleic acid molecules, which encode sPD-1 fusion proteins. In some forms, the sPD-1 fusion nucleic acid includes both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

Also disclosed are methods for treating a subject at risk of or suffering a coronavirus infection. The general effect is to induce antigen-specific protective immunity in the subject. Advantageously, the disclosed methods enhance host humoral and cell-mediated immunity. The method generally comprises administering to a subject in need of such treatment an effective amount of a fusion protein or fusion nucleic acid molecule as disclosed. In some forms, the method can be used to treat coronavirus infection. In some forms, the method can be used to reduce the risk of coronavirus infection. In some forms, the method can be used to treat an active coronavirus infection. In some forms, the coronavirus infection can be of COVID-19, SARS, or MERS. In addition, the methods can be used in the prevention and/or treatment of tumor or cancer.

Also disclosed are therapeutic or pharmaceutical compositions. In some forms, the composition comprises a therapeutically effective amount of a PD-1 fusion protein and/or a sPD-1 fusion nucleic acid molecule as disclosed and, optionally, a pharmaceutically acceptable carrier. In some forms, the therapeutic composition is a vaccine composition.

Disclosed are soluble PD-1 fusion proteins that include a soluble PD-1 protein fragment and an antigenic protein fragment. In some forms, the soluble PD-1 protein fragment includes an amino acid sequence selected from the group consisting of SEQ ID NO:1, SEQ ID NO:7, SEQ ID NO:3, SEQ ID NO:5, and SEQ ID NO:9. In some forms, the antigenic protein fragment comprises a coronavirus protein fragment.

In some forms, the coronavirus protein fragment is derived from a coronavirus receptor binding domain (RBD) or a coronavirus nucleoprotein (N). In some forms, the coronavirus protein fragment is derived from a COVID-19, a SARS, or a MERS. In some forms, the coronavirus protein fragment is derived from a COVID-19 receptor binding domain (RBD) or a COVID-19 nucleoprotein (N).

In some forms, the PD-1 fusion protein can further comprise a Fc domain.

In some forms, the PD-1 fusion protein can further comprise a linker sequence. In some forms, the linker sequence links the soluble PD-1 protein fragment and the antigenic protein fragment.

In some forms, the PD-1 fusion protein includes both an amino acid sequence selected from the group consisting of SEQ ID NO:1, SEQ ID NO:7, SEQ ID NO:3, SEQ ID NO:5, and SEQ ID NO:9 and an amino acid sequence selected from the group consisting of SEQ ID NO:11 or SEQ ID NO:12.

Also disclosed are sPD-1 fusion nucleic acid molecules encoding a PD-1 fusion protein as disclosed. In some forms, the sPD-1 fusion nucleic acid molecule comprises both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

Also disclosed are vaccine compositions comprising a sPD-1 fusion nucleic acid molecule as disclosed. Also disclosed are vaccine compositions comprising a PD-1 fusion protein as disclosed.

Also disclosed are methods for treating a subject at risk of or suffering a coronavirus infection. In some forms, the method comprises administering to the subject an effective amount of a sPD-1 fusion nucleic acid as disclosed or of a vaccine composition as disclosed. In some forms, the method comprises administering to the subject an effective amount of a PD-1 fusion protein as disclosed or of a vaccine composition as disclosed.

In some forms, the coronavirus infection is of COVID-19, SARS, or MERS. In some forms, the sPD-1 fusion nucleic acid comprises a nucleic acid fragment encoding the coronavirus protein fragment, wherein the coronavirus protein fragment is derived from a COVID-19 receptor binding domain (RBD) or a COVID-19 nucleoprotein (N), and wherein the coronavirus infection is of COVID-19.

In some forms, the sPD-1 fusion nucleic acid includes both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

In some forms, the sPD-1 fusion nucleic acid is administered by injection. In some forms, the sPD-1 fusion nucleic acid is administered via electroporation.

Also disclosed are methods for treating a subject at risk of or suffering a coronavirus infection, comprising administering to the subject an effective amount of a PD-1 fusion protein as disclosed. In some forms, the coronavirus infection is of COVID-19, SARS, or MERS. In some forms, the coronavirus protein fragment is derived from a COVID-19 receptor binding domain (RBD) or a COVID-19 nucleoprotein (N).

In some forms, the subject is at risk of a coronavirus infection. In some forms, the subject is suffering from a coronavirus infection.

Also disclosed are methods for making the disclosed PD-1 fusion proteins, sPD-1 fusion nucleic acids, and vaccine compositions. Exemplary coronavirus antigenic protein fragments include receptor binding domain (RBD) and nucleoprotein (N).

Also disclosed are pharmaceutical compositions. The pharmaceutical compositions can include the disclosed PD-1 fusion proteins or sPD-1 fusion nucleic acids. The pharmaceutical compositions typically include an effective amount of a vaccine to induce an immune response in subject in need thereof when administered to the subject. The pharmaceutical compositions can include additional agents, for example adjuvants to enhance the immune response. In some forms, the pharmaceutical compositions do not include an adjuvant. In some forms, the composition can include an effective mount of a sPD-1 fusion nucleic acid molecule that includes both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12. In some forms, the composition can include an effective mount of a PD-1 fusion protein that includes both an amino acid sequence selected from the group consisting of SEQ ID NO:1, SEQ ID NO:7, SEQ ID NO:3, SEQ ID NO:5, and SEQ ID NO:9 and an amino acid sequence selected from the group consisting of SEQ ID NO:11 or SEQ ID NO:12.

Methods of treating a subject in need thereof by administering the pharmaceutical composition to the subject are also provided. The methods can be vaccine protocols. Thus, in some forms, the subject is administered the composition to provide prophylactic or therapeutic protection against a coronavirus, such as COVID-19. The disclosed PD-1 fusion proteins and sPD-1 fusion nucleic acid molecules can be administered to a mammal in need thereof by subcutaneous (s.c.), intradermal (i.d.), intramuscular (i.m.), intravenous (i.v.), oral, or intranasal administration; or by injection or by inhalation. In some forms, the vaccine can be administered intramuscularly. The compositions containing PD-1 fusion proteins or sPD-1 fusion nucleic acid molecules are administrated to a mammal in need of protective immunity against a coronavirus infection.

BRIEF DESCRIPTION OF THE DRAWINGS

Figures 1, 2:
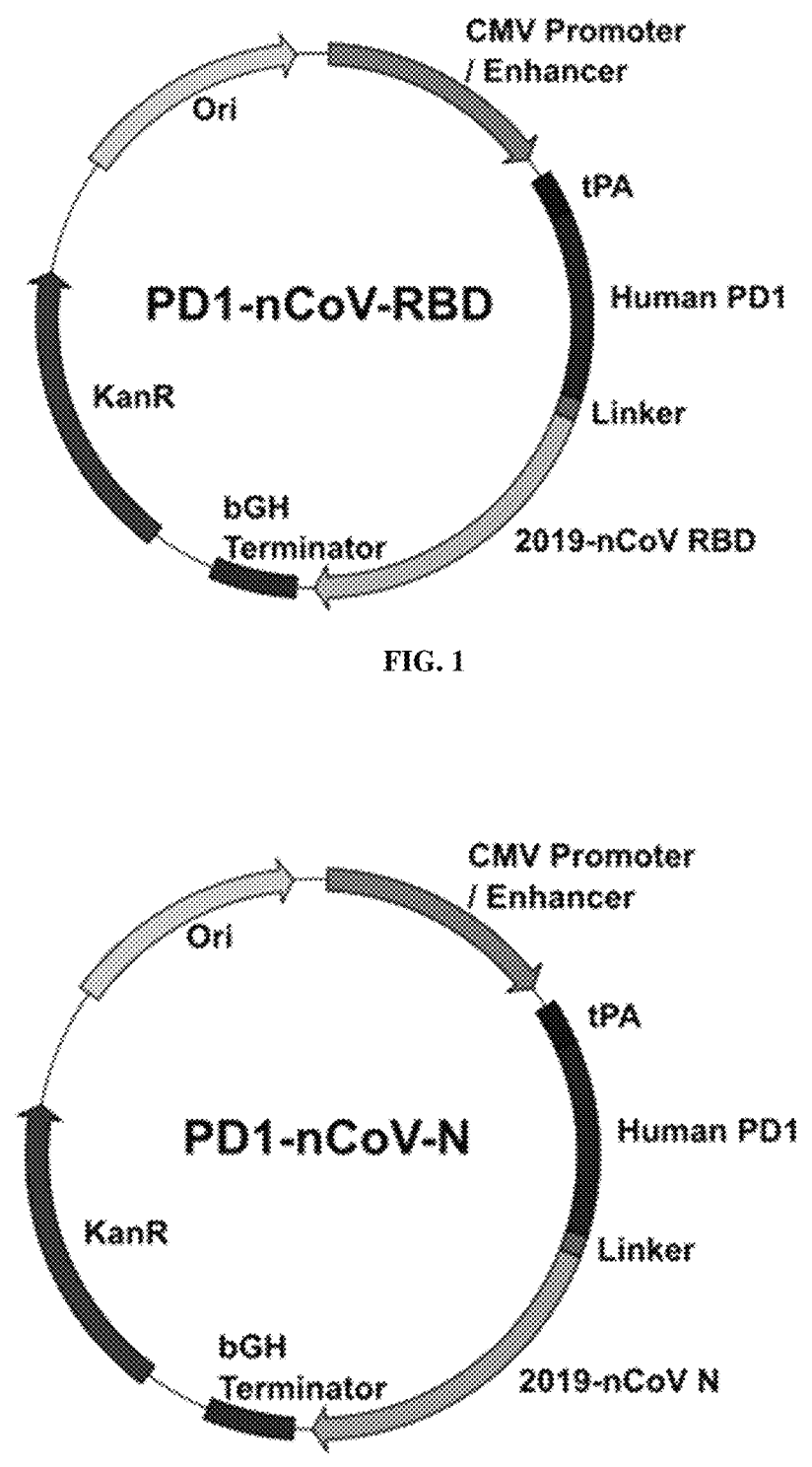

FIG. 1 is a diagram of the PD-1-nCoV-RBD DNA vaccine. This vaccine encodes for a recombinant antigen consisting of the soluble human PD-1 domain fused to the N terminus of the 2019-nCoV RBD under the control of CMV promoter/enhancer element in a pVAX plasmid backbone.

FIG. 2 is a diagram of the PD-1-nCoV-N DNA vaccine. This vaccine encodes for a recombinant antigen consisting of the soluble human PD-1 domain fused to the N terminus of the 2019-nCoV N antigen under the control of CMV promoter/enhancer element in a pVAX plasmid backbone.

BRIEF DESCRIPTION OF THE SEQUENCES

SEQ ID NO:1 is an amino acid sequence of the wild-type soluble extracellular domain of mouse PD-1 (mouse spd1).
SEQ ID NO:2 is a nucleic acid sequence of the wild-type mouse spd1 DNA.
SEQ ID NO:3 is an amino acid sequence of mspd1-14del.
SEQ ID NO:4 is a nucleic acid sequence of mspd1-14del DNA.
SEQ ID NO:5 is an amino acid sequence of mspd1-322mu.
SEQ ID NO:6 is a nucleic acid sequence of mspd1-322mu DNA.
SEQ ID NO:7 is an amino acid sequence of the wild-type soluble extracellular domain of human PD-1 (human spd1).
SEQ ID NO:8 is a nucleic acid sequence of the wild-type human spd1 DNA.
SEQ ID NO:9 is an amino acid sequence of hspd1-14del.
SEQ ID NO:10 is a nucleic acid sequence of hspd1-14del DNA.
SEQ ID NO:11 is an amino acid sequence of COVID-19 RBD protein.
SEQ ID NO:12 is an amino acid sequence of COVID-19 N protein.
SEQ ID NO:13 is an amino acid sequence of rabbit Fc domain useful to the subject invention.
SEQ ID NO:14 is a nucleic acid sequence of rabbit Fc DNA useful to the subject invention.
SEQ ID NO:15 is an amino acid sequence of a linker sequence useful according to the subject invention.
SEQ ID NO:16 is an amino acid sequence of a linker sequence useful according to the subject invention.
SEQ ID NO:17 is an amino acid sequence of a linker sequence useful according to the subject invention.
SEQ ID NO:18 is an amino acid sequence of a linker sequence useful according to the subject invention.
SEQ ID NO:19 is an amino acid sequence of a linker sequence useful according to the subject invention.
SEQ ID NO:20 is an amino acid sequence of a linker sequence useful according to the subject invention.
SEQ ID NO:21 is an amino acid sequence of a linker sequence useful according to the subject invention.
SEQ ID NO:22 is an amino acid sequence of a linker sequence useful according to the subject invention.
SEQ ID NO:23 is an amino acid sequence of a linker sequence useful according to the subject invention.
SEQ ID NO:24 is an amino acid sequence of a linker sequence useful according to the subject invention.
SEQ ID NO:25 is an amino acid sequence useful according the subject invention.
SEQ ID NO:26 is an amino acid sequence useful according the subject invention.

DETAILED DESCRIPTION OF THE INVENTION

The current outbreak of the new coronavirus (CoV), 2019-nCoV, has become a major health issue and requires immediate biomedical interventions. Rapid generation of a safe and effective vaccine to induce strong protective immunity against the virus represents one of the essential key measures to stop the spread of the infection. Disclosed here are two dendritic cell-targeting program death-1 (PD-1)-based DNA vaccines expressing 2019-nCoV receptor binding domain (RBD) and nucleoprotein (N), namely PD-1-nCoV-RBD and PD-1-nCoV-N, respectively, aiming to induce immune protection against 2019-nCoV infection in humans in both preventive and therapeutic settings.

PD-1-nCoV-RBD vaccine consists of a pVAX plasmid that encodes for a recombinant antigen consisting of human soluble PD-1 domain fused to the N terminus of nCoV RBD. Similarly, PD-1-nCoV-N vaccine is also in a pVAX plasmid backbone and has a gene expression cassette that encodes for a recombinant antigen of a human soluble PD-1 domain fused to the N terminus of nCoV N protein.

Once immunized with these vaccines, recombinant PD-1-tagged antigens are produced in the vaccines. The soluble PD-1 domain on the antigens will binds to PD-1 ligands constitutively expressed on professional antigen-presenting cells, such as dendritic cells. This will lead to better antigen uptake and presentation by dendritic cells, resulting in enhanced induction of antibody and T cell immune responses. The utility of PD-1-based DNA vaccines using different antigens has been demonstrated earlier (U.S. Pat. No. 9,029,315). This platform has been applied in the design and generation of the disclosed new coronavirus-specific antigenic constructs. These PD-1-based vaccines are used to induce neutralizing antibody and T cell responses in hosts to prevent and/or control CoV infection. The underlying DNA vaccine vector has been shown to be safe and there is no issue of preexisting immunity against the vaccine vector used. In addition, the immunity generated by the disclosed vaccines should also have minimal adverse effects, including antibody-dependent enhancement of infection.

There are currently no approved vaccines in the market for 2019-nCoV or other coronaviruses.

At present, there is no approved prevent or therapeutic vaccines available for 2019-nCoV or other types of coronavirus.

According to the media, multiple research teams and companies, both locally and internationally, are trying to generate vaccines against 2019-nCoV using different types of vectors, including influenza A virus vector, adenoviral vector, mRNA-based vaccine, etc. However, there is no publication on the immunogenicity or efficacy of any of these vaccines.

The disclosed materials and methods solve the problems of (1) the major outbreak of 2019-nCoV infection, (2) the lack of a protective vaccine available for the 2019-nCoV virus, and (3) the lack of an effective treatment available to treat 2019-nCoV-infected patients. These problems are solved by, for example, the disclosed PD-1-based 2019-nCoV vaccines, PD-1-nCoV-RBD and PD-1-nCoV-N, which can be used as preventive measures to elicit protective immunity in healthy hosts and/or can be used as a therapeutic measure to help controlling viral loads and associated pathology in infected patients.

Development and production of the disclosed DNA vaccines can be facilitated by, for example, testing the vaccines in vitro for their ability to generate the recombinant PD-1-fused antigens in mammalian cell lines and for the ability of these antigens to bind to PD-1 ligands; examining their safety, immunogenicity and protective efficacy in animal models, including, but not limited to, mice and rhesus macaques; and manufacture of GMP-grade vaccines in large quantity for preclinical evaluation and clinical testing.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an antigen is disclosed and discussed and a number of modifications that can be made to a number of molecules or compositions including the antigen are discussed, each and every combination and permutation of the antigen and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

As used herein, the term "adjuvant" refers to a compound or mixture that enhances an immune response.

As used herein, "autologous" means derived from self.

The term "child" is meant to be a person or a mammal between 0 months and 18 years of age and "young child" refers to a child <5 yrs. old.

As used herein, the term "effective amount" or "therapeutically effective amount" means a dosage sufficient to treat, inhibit, or alleviate one or more symptoms of a disease state being treated or to otherwise provide a desired pharmacologic effect. The precise dosage will vary according to a variety of factors such as subject-dependent variables (e.g., age, immune system health, etc.), the disease, and the age of the subject.

As used herein, the term "gene" refers to a nucleic acid (e.g., DNA or RNA) sequence that including coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The term "gene" encompasses both cDNA and genomic forms of a gene, which may be made of DNA, or RNA. A genomic form or clone of a gene may contain the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "immunogenic" or "antigenic" in connection with a protein or composition means that the protein or composition can induce an immune response and is therefore antigenic. By "immune response" means any reaction by the immune system. These reactions include the alteration in the activity of an organism's immune system in response to an antigen and can involve, for example, antibody production, induction of cell-mediated immunity, complement activation, or development of immunological tolerance.

The term "nasal administration" refers to any form of administration whereby an active ingredient is propelled or otherwise introduced into the nasal passages of a subject so that it contacts the respiratory epithelium of the nasal cavity, from which it is absorbed into the systemic circulation. Nasal administration can also involve contacting the olfactory epithelium, which is located at the top of the nasal cavity between the central nasal septum and the lateral wall of each main nasal passage. The region of the nasal cavity immediately surrounding the olfactory epithelium is free of airflow. Thus, specialized methods must typically be employed to achieve significant absorption across the olfactory epithelium.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein.

The term "mammal" as used herein includes both humans and non-humans and include but is not limited to humans, non-human primates, canines, felines, murines, bovines, equines, and porcines.

The term "topical administration" refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration can result in a limited distribution of the agent to the skin and surrounding tissues or, when the agent is removed from the treatment area by the bloodstream, systemic distribution of the agent. In a preferred form, the agent is delivered by transdermal delivery, e.g., using a transdermal patch. Transdermal delivery refers to the diffusion of an agent across the skin (stratum corneum and epidermis), which acts as a barrier few agents are able to penetrate. In contrast, the dermis is permeable to absorption of many solutes and drugs, and topical administration therefor occurs more readily through skin that is abraded or otherwise stripped of the epidermis to expose the dermis. Absorption through intact skin can be enhanced by combining the active agent with an oily vehicle (e.g., creams, emollients, penetration enhancers, and the like, as described, e.g., in Remington's Pharmaceutical Sciences, current edition, Gennaro et al., eds.) prior to application to the skin (a process known as inunction).

As used herein, the term "peptide" refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

As used herein "recombinant DNA" a refers to DNA molecules that is extracted from different sources and chemically joined together; for example DNA including a gene from one source may be recombined with DNA from another source. Recombinant DNA can be all heterologous DNA or a combination of homologous and heterologous DNA. The recombinant DNA can be integrated into and expressed from a cell's chromosome, or can be expressed for an extra-chromosomal array such as a plasmid.

As used herein, a "variant," "mutant," or "mutated" polynucleotide or polypeptide contains at least one polynucleotide or polypeptide sequence alteration as compared to the polynucleotide or polypeptide sequence of the corresponding wild-type or parent polynucleotide or polypeptide. Mutations may be natural, deliberate, or accidental. Mutations include substitutions, deletions, and insertions.

B. Compositions

Disclosed are soluble PD-1 (sPD-1) proteins and nucleic acids, and therapeutic compositions comprising soluble PD-1 proteins and nucleic acids, useful for inducing antigen-specific protective immunity against coronavirus infection. In some forms, the subject sPD-1 proteins, nucleic acids, and compositions are formulated as a vaccine composition. In some forms, the fusion proteins can be mspd1-nCoV-RBD, mspd1-14del-nCoV-RBD, mspd1-322mu-nCoV-RBD, hspd1-14del-nCoV-RBD, mspd1-nCoV-N, mspd1-14del-nCoV-N, mspd1-322mu-nCoV-N, and hspd1-14del-nCoV-N, and nucleic acid molecules encoding these fusion proteins.

The disclosed compositions and methods make use of the down-regulation of virus-specific $CD8^+$ T cells responses by the immune regulatory PD-1/PD-L pathway. In particular, variants of PD-1 that does not interact with either PD-L1 or PD-L2 (the ligands of PD-1) are employed.

In some forms, the disclosed vaccines are designed to mimics the binding of programmed death-1 (PD-1) to its ligands expressed on dendritic cells (DCs) for functional activation, by fusing soluble PD-1 with an antigen of coronavirus. In some forms, the disclosed fusion DNA vaccines can elicit robust anti-antigen antibody titers, including both IgG1 (Th2) and IgG2a (Th1) responses. High frequencies of antigen-specific, broadly reactive and polyfunctional T cells, especially $CD8^+$ T cells, can be elicited following immunization. In some forms, the responses can be dose-dependent and long lasting. Thus, soluble PD-1-based vaccination offers an easy, repeatable, and effective way to induce durable and protective CD8+ cell immunity against coronavirus, which has important implications for coronavirus vaccine development.

In some forms, the mspd1-14del protein variant is obtained by deleting amino acids 26-39 of the wild-type mspd1 Amino acids 26-39 are the first 14 amino acids encoded by the second exon of the wild-type mouse PD-1 gene. These 14 amino acids of mspd1 have the same sequence as the first 14 amino acids encoded by the second exon of the human hspd1-14del homologue. The mspd1-322mu protein variant is obtained by changing amino acid residue 108 of the wild-type PD-1 protein from Met to Val. The hspd1-14del variant, which is derived from a natural isoform of human PD-1, has a deletion of amino acids 26-39 of the wild-type hspd1 (encoded by the first part of the second exon of the wild-type human PD-1 gene).

mspd1 fusion proteins bind to PD-1 ligands PD-L1 and PD-L2, and the binding of PD-1 to PD-L can be blocked by anti-PD-L1/L2 antibodies. It is postulated that the binding of mspd1 fusion proteins inhibits the PD-1/PD-L pathway, which transmits negative signals to immune cells. In comparison, none of mspd1-14del, mspd1-322mu, and hspd1-14del fusion proteins binds to PD-L1 or PD-L2. This indicates that amino acid residues 26-39 encoded by DNA in exon 2 of sPD-1 and amino acid residue 108 Met of msPD-1 are important for PD-L binding.

Advantageously, the administration of mspd1, mspd1-14del, mspd1-322mu, and hspd1-14del fusion proteins, or fusion DNA thereof, can enhanced antigen-specific immune responses.

C. PD-1 Variants and Fusion Constructs

The disclosed fusion proteins can use sPD-1 protein variants. In some forms, the sPD-1 protein variant is obtained by deleting amino acid residues 26-39 of a wild-type sPD-1 protein. The wild-type sPD-1 protein is preferably of mammalian origin (such as a wild-type mouse, rabbit, non-human primates, or pig PD-1 protein), more preferably, of human origin.

In some forms, the sPD-1 protein variant is mspd1-14del, which has an amino acid sequence comprising SEQ ID NO:3. In some forms, the sPD-1 protein variant is mspd1-322mu, which has an amino acid sequence comprising SEQ ID NO:5. In some forms, the sPD-1 protein variant is hspd1-14del, which has an amino acid sequence comprising SEQ ID NO:9.

In some forms, the PD-1 protein variants can be homologous to mspd1-14del (SEQ ID NO:3), mspd1-322mu (SEQ ID NO:5), or hspd1-14del (SEQ ID NO:9). In some forms, the sPD-1 protein variant has an amino acid sequence that is at least about 95%, 96%, 97%, 98%, 99%, or 99.5% identical to SEQ ID NO:3. In some forms, the sPD-1 protein variant has an amino acid sequence that is at least about 95%, 96%, 97%, 98%, 99%, or 99.5% identical to SEQ ID NO:5. In some forms, the sPD-1 protein variant has an amino acid sequence that is at least about 95%, 96%, 97%, 98%, 99%, or 99.5% identical to SEQ ID NO:9.

Also disclosed are nucleic acid molecules that encode the sPD-1 proteins as disclosed. The nucleic acid molecules encompass DNA molecules (e.g., genomic DNA and cDNA) and RNA molecules. In addition, the disclosed nucleic acid molecules may be single-stranded or double-stranded.

In some forms, the nucleic acid molecule encodes a sPD-1 protein, which is obtained by deleting amino acid residues 26-39 of a wild-type sPD-1 protein (such as a wild-type human, mouse, or rabbit sPD-1 protein). In some forms, the nucleic acid molecule encodes mspd1-14del, and has a sequence comprising SEQ ID NO:4. In some forms, the subject nucleic acid molecule encodes mspd1-322mu, and has a sequence comprising SEQ ID NO:6. In some forms, the subject nucleic acid molecule encodes hspd1-14del, and has a sequence comprising SEQ ID NO:10.

In some forms, the nucleic acid molecules can be homologous to nucleic acids encoding mspd1-14del, mspd1-322mu, or hspd1-14del. In some forms, the nucleic acid molecule has a sequence that is at least about 95%, 96%, 97%, 98%, 99%, or 99.5% identical to SEQ ID NO:4, SEQ ID NO:6, or SEQ ID NO:10.

Also disclosed are PD-1 fusion proteins. In some forms, the PD-1 fusion proteins can comprise a sPD-1 protein fragment fused with an antigenic protein fragment, where the antigenic protein fragment is a coronavirus protein fragment. In some forms, the sPD-1 fusion protein comprises a Fc domain. In some forms, the soluble PD-1 protein is linked to the antigen via a linker sequence. In some forms, the PD-1 fusion protein comprises a PD-1 protein fused with a Fc domain, optionally via a linker sequence.

In some forms, the sPD-1 fusion protein comprises the wild-type mouse soluble PD-1 protein (mspd), which has an amino acid sequence comprising SEQ ID NO:1. In some forms, the sPD-1 fusion protein comprises the wild-type human sPD-1 protein (hspd1), which has an amino acid sequence comprising SEQ ID NO:7. In some forms, the sPD-1 fusion protein is a variant mouse sPD-1 protein mspd1-14del, which has an amino acid sequence comprising SEQ ID NO:3. In some forms, the sPD-1 fusion protein is a variant mouse sPD-1 protein mspd1-322mu, which has an amino acid sequence comprising SEQ ID NO:5. In some forms, the sPD-1 protein is a variant human sPD-1 protein (hspd1-14del), and has an amino acid sequence comprising SEQ ID NO:9.

The antigenic protein fragment can be derived from any coronavirus protein from any coronavirus strain. Preferably, the coronavirus strain is COVID-19, SARS, or MERS. Preferably, the coronavirus protein fragment is derived from coronavirus RBD or N.

In some forms, the soluble PD-1, its variants, and fusion proteins thereof serve as molecular or protein adjuvants to enhance immune response. Additionally, nucleic acid molecules encoding the soluble PD-1, its variants, and fusion proteins thereof can also be administered to a subject to enhance immune response.

In some forms, the antigenic protein fragment is derived from an immunogenic fragment of a coronavirus protein domain including, but not limited to, RBD and N. In some forms, the antigen protein is derived from COVID-19 RBD or COVID-19 N. In some forms, the antigen protein comprises SEQ ID NO:11 or SEQ ID NO:12. In some forms, the sPD-1 fusion protein further comprises a Fc domain. In some forms, the sPD-1 fusion protein comprises a rabbit Fc domain for protein purification purpose.

The term "Fc domain" encompasses the full length and fragments of native human and animal Fc and Fc variant molecules and sequences, including for example, IgG, IgM, IgD, IgE, IgA and subtypes such as for example IgG1, IgG2, IgG3, IgG4, IgA1, and IgA2. As with Fc variants and native Fc's, the term "Fc domain" includes molecules in monomeric or multimeric form, whether digested from whole antibody or produced by other means.

The term "Fc variant" refers to a molecule or sequence that is modified from a native Fc but still comprises a binding site for the salvage receptor. Fc domains include molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The Fc domain can be of antibodies of any isotype, including IgG, IgA, IgE, IgD, and IgM. IgG isotype antibodies can be further subdivided into IgG1, IG2, IgG3, and IgG4 subtypes. IgA antibodies can be further subdivided into IgA1 and IgA2 subtypes. In some forms, the Fc domain is IgG1.

In some forms, the sPD-1 fusion protein comprises a linker sequence that links the soluble PD-1 domain to the antigen. In addition, the Fc domain can also be linked to the fusion protein via a linker sequence. Linker sequence is typically a peptide chain. The length of the peptide may be, for example, 6, 7, 8, 9, 10, 11, 12, 13, 14, 15, 16, 17, 18, 19, 20, 21, 22, 23, 24, 25, 30, 40, 50 or more amino acid residues, but typically is between 5 and 25 residues.

Depending upon the length and side chain composition, a linker may have, but need not have, greater than average flexibility. Flexibility can be calculated using algorithms known in the art. In some forms, the linker sequence is SEQ ID NO:15. Examples of useful linkers include, but are not limited to, 9Gly (SEQ ID NO:16), 9Glu (SEQ ID NO:17), 9Ser (SEQ ID NO:18), 5GlyCys2ProCys (SEQ ID NO:19), 4Gly3Ser (SEQ ID NO:20), Ser Cys Val Pro Leu Met Arg Cys Gly Cys Asn (SEQ ID NO:21), Pro Ser Cys Val Pro Leu Met Arg Cys Gly Cys Asn (SEQ ID NO:22), Gly Asp Leu Ile Tyr Arg Asn Gln Lys (SEQ ID NO:23), and 9GlyProSerCysValProLeuMetArgCysGlyGlyCysCysAsn (SEQ ID NO:24).

In some forms, the subject sPD-1 fusion protein comprises PD-1-CoV-RBD or PD-1-CoV-N.

Also disclosed are sPD-1 fusion nucleic acid constructs comprise a nucleic acid molecule encoding a disclosed sPD-1 fusion protein. In some forms, the sPD-1 fusion construct comprises a nucleic acid molecule encoding a sPD-1 protein fused with a nucleic acid encoding a coronavirus antigen. In some forms, the PD-1 fusion construct comprises a Fc DNA. In some forms, the soluble PD-1 DNA is linked to the antigen DNA via a linker sequence. Optionally, the Fc DNA is linked to the sPD-1-antigen DNA via a linker DNA sequence.

The disclosed antigenic nucleic acid molecule of the subject invention encodes immunogenic fragments of coronavirus.

In some forms, the antigenic nucleic acid molecule encodes a coronavirus antigen. In some forms, the encoded coronavirus antigen is COVID-19 RBD (SEQ ID NO:11). In some forms, the encoded coronavirus antigen is COVID-19 N (SEQ ID NO:12).

In some forms, the fusion nucleic acid molecule comprises the wild-type mouse PD-1 (mspd1) DNA (SEQ ID NO:2). In some forms, the fusion nucleic acid molecule comprises the wild-type human PD-1 (hspd1) DNA (SEQ ID NO:8). In some forms, the fusion nucleic acid molecule comprises a variant mouse PD-1 DNA that has a sequence of SEQ ID NO:4 or SEQ ID NO:6. In some forms, the fusion nucleic acid molecule comprises a variant human PD-1 DNA that has a sequence of SEQ ID NO:10.

In some forms, the disclosed PD-1 fusion protein or sPD-1 fusion nucleic acid is typically substantially free of other components, such as other biological molecules, proteins or peptides, nucleic acids, lipids and carbohydrates. The term "substantially free of," as used herein, encompasses preparations of materials, such as the disclosed proteins, compounds, and nucleic acids, having less than about 20%, 10% and preferably less than 5% (by dry weight) contaminating factors (such as biological molecules, proteins or peptides, nucleic acids, lipids and carbohydrates and other cellular components).

If desired, the disclosed proteins and nucleic acid molecules can be modified by any suitable process. Strategies for protein optimization are sometimes carried out using random mutagenesis. In these cases, positions are chosen randomly, or amino acid changes are made using simplistic rules. For example, all residues may be mutated to alanine, referred to as alanine scanning. In addition, substitution of amino acids other than those specifically exemplified or naturally present in a fusion protein are also contemplated. For example, non-natural amino acids can be substituted for the amino acids of the fusion protein, so long as the fusion protein having the substituted amino acids retains substantially the same functional activity as the fusion protein in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, alpha-amino isobutyric acid, 4-aminobutyric acid, 2-amino butyric acid, gamma-amino butyric acid, epsilon-amino hexanoic acid, 6-amino hexanoic acid, 2-amino isobutyric acid, 3-amino propionic acid, norleucine, norvaline, sarcosine, homocitrulline, cysteic acid, tau-butylglycine, tau-butylalanine, phenylglycine, cyclohexylalanine, beta-alanine, fluoro-amino acids, designer amino acids such as beta-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The disclosed nucleic acid molecules can be variants of nucleic acid molecules that encode functional fusion proteins. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, word-length=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The disclosed nucleic acid molecules can have sequences that are sufficiently homologous with the disclosed nucleic acid sequences so as to permit hybridization with that sequence under standard stringent conditions and standard methods (Maniatis et al., 1982). As used herein, "stringent" conditions for hybridization refers to conditions wherein hybridization is typically carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983): Tm=81.5 C+16.6 Log [Na+]+0.41(% G+C)−0.61(% formamide)−600/length of duplex in base pairs.

Washes are typically carried out as follows:
(1) Twice at room temperature for 15 minutes in 1×SSPE, 0.1% SDS (low stringency wash).
(2) Once at Tm−20° C. for 15 minutes in 0.2×SSPE, 0.1% SDS (moderate stringency wash).

Also disclosed are expression constructs comprising PD-1 nucleic acid molecules or fusion constructs thereof. The disclosed expression constructs generally include regulatory elements that are functional in the intended host cell in which the expression construct is to be expressed. Regulatory elements include promoters, transcription termination sequences, translation termination sequences, enhancers, and polyadenylation elements.

The expression construct can comprise a promoter sequence operably linked to a nucleic acid sequence encoding a peptide, such a soluble PD-1 fusion protein. Multiple copies of promoters or multiple promoters can be used in the expression construct. In some forms, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, the expression construct can comprise suitable promoters that can drive transcription of the polynucleotide sequence. For mammalian cells, suitable promoters include for example, Pcmv, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMPS promoter, and TRP-1 promoter.

1. Adjuvants

The disclosed compositions and vaccines can be administered in conjunction with other immunoregulatory agents, including adjuvants. Useful adjuvants but are not limited to, one or more set forth below:

Mineral Containing Adjuvant Compositions include mineral salts, such as aluminum salts and calcium salts. Exemplary mineral salts include hydroxides (e.g., oxyhydroxides), phosphates (e.g., hydroxyphosphates, orthophosphates), sulfates, and the like or mixtures of different mineral compounds (e.g., a mixture of a phosphate and a hydroxide adjuvant, optionally with an excess of the phosphate), with the compounds taking any suitable form (e.g., gel, crystalline, amorphous, and the like), and with adsorption to the salt(s) being preferred. The mineral containing compositions can also be formulated as a particle of metal salt (WO/0023105). Aluminum salts can be included in compositions such that the dose of $Al^{3+}$ is between 0.2 and 1.0 mg per dose.

Oil-Emulsion Adjuvants suitable for use as adjuvants can include squalene-water emulsions, such as MF59 (5% Squalene, 0.5% Tween 80, and 0.5% Span 85, formulated into submicron particles using a microfluidizer). See, e.g., WO90/14837 and Podda, Vaccine 19: 2673-2680, 2001. Additional adjuvants for use in the compositions are submicron oil-in-water emulsions. Examples of submicron oil-in-water emulsions for use herein include squalene/water emulsions optionally containing varying amounts of MTP-PE, such as a submicron oil-in-water emulsion containing 4-5% w/v squalene, 0.25-1.0% w/v Tween 80 (polyoxyelthylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-s-n-glycero-3-huydroxyphosphophoryloxy)-ethylamine (MTP-PE), for example, the submicron oil-in-water emulsion known as "MF59" (International Publication No. WO90/14837; U.S. Pat. Nos. 6,299,884 and 6,451,325, incorporated herein by reference in their entirety. MF59 can contain 4-5% w/v Squalene (e.g., 4.3%), 0.25-0.5% w/v Tween 80, and 0.5% w/v Span 85 and optionally contains various amounts of MTP-PE, formulated into submicron particles using a microfluidizer such as Model 110Y microfluidizer (Microfluidics, Newton, Mass.). For example, MTP-PE can be present in an amount of about 0-500 µg/dose, or 0-250 µg/dose, or 0-100 µg/dose. Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) can also be used as adjuvants.

Saponin Adjuvant Formulations can also be used as adjuvants. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), Gypsophilla *paniculata* (brides veil), and *Saponaria officianalis* (soap root). Saponin adjuvant formulations can include purified formulations, such as QS21, as well as lipid formulations, such as Immunostimulating Complexes (ISCOMs; see below). Saponin compositions have been purified using High Performance Thin Layer Chromatography (HPLC) and Reversed Phase High Performance Liquid Chromatography (RP-HPLC). Specific purified fractions using these techniques have been identified, including QS7, QS17, QS18, QS21, QH-A, QH-B and QH-C. A method of production of QS21 is disclosed in U.S. Pat. No. 5,057,540. Saponin formulations can also comprise a sterol, such as cholesterol (see WO96/33739). Combinations of saponins and cholesterols can be used to form unique particles called ISCOMs. ISCOMs typically also include a phospholipid such as phosphatidylethanolamine or phosphatidylcholine. Any known saponin can be used in ISCOMs. For example, an ISCOM can include one or more of Quil A, QHA and QHC. ISCOMs are described in EP0109942, WO96/11711, and WO96/33739. Optionally, the ISCOMS can be devoid of additional detergent. See WO00/07621. A description of the development of saponin based adjuvants can be found at Barr, et al., "ISCOMs and other saponin based adjuvants", Advanced Drug Delivery Reviews 32: 247-27, 1998. See also Sjolander, et al., "Uptake and adjuvant activity of orally delivered saponin and ISCOM vaccines", *Advanced Drug Delivery Reviews* 32: 321-338, 1998.

Virosomes and Virus Like Particles (VLPs) can also be used as adjuvants. These structures generally contain one or more proteins from a virus optionally combined or formulated with a phospholipid. They are generally non-pathogenic, non-replicating and generally do not contain any of the native viral genome. The viral proteins can be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein pl).

Bacterial or Microbial Derivatives useful as adjuvants include: (i) Non-Toxic Derivatives of Enterobacterial Lipopolysaccharide (LPS); (ii) lipid derivatives, (iii) immunostimulatory oligonucleotides and ADP-Ribosylating Toxins and Detoxified Derivatives Thereof, (iv) ADP-Ribosylating Toxins and Detoxified Derivatives Thereof. Examples of Non-Toxic Derivatives of LPS Monophosphoryl lipid A (MPL) and 3-O-deacylated MPL (3 dMPL). 3 dMPL is a mixture of 3 De-O-acylated monophosphoryl lipid A with 4, 5, or 6 acylated chains. An example of a "small particle" form of 3 De-O-acylated monophosphoryl lipid A is disclosed in EP 0 689 454. Such "small particles" of 3 dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529 (Johnson et al., Bioorg Med Chem Lett, 9: 2273-2278, 1999). Examples of lipid A derivatives can include derivatives of lipid A from *Escherichia coli* such as OM-174. OM-174 is described for example in Meraldi et al., Vaccine 21: 2485-2491, 2003; and Pajak, et al., Vaccine 21: 836-842, 2003. Examples of immunostimulatory oligonucleotides nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine can be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", *Nucleic Acids Research* 31: 2393-2400, 2003; WO02/26757 and WO99/62923 for examples of analog substitutions. The adjuvant effect of CpG oligonucleotides is further discussed in Krieg, Nature Medicine (2003) 9(7): 831-835; McCluskie, et al., *FEMS Immunology and Medical Microbiology* (2002) 32:179-185; WO98/40100; U.S. Pat. Nos. 6,207,646; 6,239,116 and 6,429,199. The CpG sequence can be directed to Toll-like receptor (TLR9), such as the motif GTCGTT or TTCGTT. See Kandimalla, et al., "*Toll-like receptor* 9: modulation of recognition and cytokine induction by novel synthetic CpG DNAs", *Biochemical Society Transactions* (2003) 31 (part 3): 654-658. The CpG sequence can be specific for inducing a Th1 immune response, such as a CpG-A ODN, or it can be more specific for inducing a B cell response, such a CpG-B ODN. CpG-A and CpG-B ODNs are discussed in Blackwell, et al., *J. Immunol.* 170: 4061-4068, 2003; Krieg, *TRENDS in Immunology* 23: 64-65, 2002, and WO01/95935. In some aspects, the CpG oligonucleotide can be constructed so that the 5' end is accessible for receptor recognition. Optionally, two CpG oligonucleotide sequences can be attached at their 3' ends to form "immunomers". See, for example, Kandimalla, et al., *BBRC* 306: 948-95, 2003; Kandimalla, et al., *Biochemical Society Transactions* 31: 664-658, 2003; Bhagat et al.," *BBRC* 300: 853-861, 2003, and WO03/035836. Bacterial ADP-ribosylating toxins and detoxified derivatives thereof can be used as adjuvants. For example, the toxin can be derived from *E. coli* (i.e., *E. coli* heat labile enterotoxin (LT)), cholera (CT), or pertussis (PTX). The use of detoxified ADP-ribosylating toxins as mucosal adjuvants is described in WO95/17211 and as parenteral adjuvants in WO98/42375. In some aspects, the adjuvant can be a detoxified LT mutant such as LT-K63, LT-R72, and LTR192G. The use of ADP-ribosylating toxins and detoxified derivatives thereof, particularly LT-K63 and LT-R72, as adjuvants can be found in the following references, each of which is specifically incorporated by reference herein in their entirety: Beignon, et al., *Infection and Immunity* 70: 3012-3019, 2002; Pizza, et al., *Vaccine* 19: 2534-2541, 2001; Pizza, et al., *Int. J. Med. Microbiol* 290: 455-461, 2003; Scharton-Kersten et al., *Infection and Immunity* 68: 5306-5313, 2000; Ryan et al., *Infection and Immunity* 67: 6270-6280, 2003; Partidos et al., *Immunol. Lett.* 67: 09-216, 1999; Peppoloni et al., *Vaccines* 2: 285-293, 2003; and Pine et al., *J. Control Release* 85: 263-270, 2002.

Bioadhesives and mucoadhesives can also be used as adjuvants. Suitable bioadhesives can include esterified hyaluronic acid microspheres (Singh et al., *J. Cont. Rel.* 70:267-276, 2001) or mucoadhesives such as cross-linked derivatives of poly(acrylic acid), polyvinyl alcohol, polyvinyl pyrollidone, polysaccharides and carboxymethylcellulose. Chitosan and derivatives thereof disclosed, for example, in WO99/27960, can also be used as adjuvants.

Adjuvant Microparticles: Microparticles can also be used as adjuvants. Microparticles (i.e., a particle of about 100 nm to about 150 μm in diameter, or 200 nm to about 30 μm in diameter, or about 500 nm to about 10 μm in diameter) formed from materials that are biodegradable and/or non-toxic (e.g., a poly(alpha-hydroxy acid), a polyhydroxybutyric acid, a polyorthoester, a polyanhydride, a polycaprolactone, and the like), with poly(lactide-co-glycolide) are envisioned, optionally treated to have a negatively-charged surface (e.g., with SDS) or a positively-charged surface (e.g., with a cationic detergent, such as CTAB).

Examples of liposome formulations suitable for use as adjuvants are described in U.S. Pat. Nos. 6,090,406, 5,916, 588, and EP 0 626 169. Additional adjuvants include polyoxyethylene ethers and polyoxyethylene esters. WO99/52549. Such formulations can further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). In some aspects, polyoxyethylene ethers can include: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, or polyoxyethylene-23-lauryl ether. PCPP formulations for use as adjuvants are described, for example, in Andrianov et al., Biomaterials 19: 109-115, 1998.1998. Examples of muramyl peptides suitable for use as adjuvants can include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphoryloxy)-ethylamine MTP-PE). Examples of imidazoquinolone compounds suitable for use as adjuvants can include Imiquimod and its homologues, described further in Stanley, "Imiquimod and the imidazoquinolones: mechanism of action and therapeutic potential" Clin Exp Dermatol 27: 571-577, 2002 and Jones, "Resiquimod 3M", Curr Opin Investig Drugs 4: 214-218, 2003. Human immunomodulators suitable for use as adjuvants can include cytokines, such as interleukins (e.g., IL-1, IL-2, IL-4, IL-5, IL-6, IL-7, IL-12, and the like), interferons (e.g., interferon-gamma), macrophage colony stimulating factor, and tumor necrosis factor.

Adjuvant Combinations: The adjuvants are used in some preferred forms as combinations. For example, adjuvant compositions can include: a saponin and an oil-in-water emulsion (WO99/11241); a saponin (e.g., QS21)+a non-toxic LPS derivative (e.g., 3 dMPL) (see WO94/00153); a saponin (e.g., QS21)+a non-toxic LPS derivative (e.g., 3 dMPL)+a cholesterol; a saponin (e.g., QS21)+3 dMPL+IL-12 (optionally+a sterol) (WO98/57659); combinations of 3 dMPL with, for example, QS21 and/or oil-in-water emulsions (See European patent applications 0835318, 0735898 and 0761231); SAF, containing 10% Squalane, 0.4% Tween 80, 5% pluronic-block polymer L121, and thr-MDP, either microfluidized into a submicron emulsion or vortexed to generate a larger particle size emulsion. Ribi adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox); and one or more mineral salts (such as an aluminum salt)+a non-toxic derivative of LPS (such as 3 dPML).

Aluminum salts and MF59 are examples of adjuvants for use with injectable influenza vaccines. Bacterial toxins and bioadhesives are examples of adjuvants for use with mucosally-delivered vaccines, such as nasal vaccines. All adjuvants noted above and others as generally known in the art to one of ordinary skill can be formulated for intranasal administration using techniques well known in the art.

2. Formulations and Carriers

The disclosed compositions can be formulated in pharmaceutical compositions. These compositions can comprise, in addition to one or more of the disclosed fusion proteins or nucleic acid molecules, a pharmaceutically acceptable excipient, carrier, buffer, stabilizer, or other materials well known to those skilled in the art. Such materials should typically be non-toxic and should not typically interfere with the efficacy of the active ingredient. The precise nature of the carrier or other material can depend on the route of administration, e.g., oral, intravenous, cutaneous or subcutaneous, nasal, intramuscular, or intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil, or synthetic oil. Physiological saline solution, dextrose, or other saccharide solution or glycols such as ethylene glycol, propylene glycol, or polyethylene glycol can be included. The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, ethanol and the like. Examples of suitable pharmaceutical carriers are described in "Remington's Pharmaceutical Sciences" by E. W. Martin. The formulation should be selected according to the mode of administration.

For intravenous, cutaneous, or subcutaneous injection, or injection at the site of affliction, the active ingredient will be in the form of a parenterally acceptable aqueous solution which is pyrogen-free and has suitable pH, isotonicity, and stability. Those of relevant skill in the art are well able to prepare suitable solutions using, for example, isotonic vehicles such as Sodium Chloride Injection, Ringer's Injection, or Lactated Ringer's Injection. Preservatives, stabilizers, buffers, antioxidants, and/or other additives can be included, as required.

Administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in the latest edition of Remington's Pharmaceutical Science, Mack Publishing Company, Easton, Pa. ("Remington's").

Also disclosed are therapeutic or pharmaceutical compositions. In some forms, the composition comprises a therapeutically effective amount of a protein and/or nucleic acid molecule as disclosed and, optionally, a pharmaceutically acceptable carrier.

In some forms, the proteins and/or nucleic acid molecules are formulated into a vaccine composition for administration to subjects having certain risks of coronavirus infection. A vaccine composition is an antigenic preparation that comprises one or more immunogenic antigens used to produce active immunity to a disease. In addition, the disclosed compositions can be administered to a subject with an existing coronavirus infection. Such treatments can provide for customized vaccine schedules and compositions to prevent or minimize worsening of the diseases.

Also disclosed are therapeutic compositions useful for practicing the therapeutic methods described herein. The therapeutic composition can be any form of pharmaceutical format, including injectable formulations such as liquid and lyophilized injections.

In some forms, a therapeutically effective amount of a protein and/or nucleic acid molecule as disclosed is typically an amount such that when administered in a physiologically tolerable composition is sufficient to achieve a plasma concentration of from about 0.01 microgram (μg) per milliliter (mL) to about 200 μg/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Suitable non-toxic pharmaceutically acceptable carriers for use with the agent will be apparent to those skilled in the art of pharmaceutical formulation. See, for example, Remington's Pharmaceutical Sciences, latest edition, ed. Alfonso R. Gennaro, Mack Publishing Company, Easton, Pa. Suitable carriers include ethanol, dimethyl sulfoxide, glycerol, silica, alumina, starch, sorbitol, inositol, xylitol, D-xylose, mannitol, powdered cellulose, microcrystalline cellulose, talc, colloidal silicon dioxide, calcium carbonate, magnesium carbonate, calcium phosphate, calcium aluminum silicate, aluminum hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The therapeutic composition, if desired, can also contain minor amounts of wetting or emulsifying agents, or pH buffering agents. In addition, if desired, the composition can contain minor amounts of auxiliary substances such as wetting or emulsifying agents, pH buffering agents and the like which enhance the effectiveness of the active ingredient.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80%, or about 30% to about 70%, active ingredient (w/w).

The preparation of a pharmacological composition that contains active ingredients dissolved or dispersed therein is well understood in the art and need not be limited based on formulation. Typically, such compositions are prepared as injectables either as liquid solutions or suspensions; however, solid forms suitable for solution, or suspensions, in liquid prior to use also can be prepared. The preparation also can be emulsified.

The disclosed therapeutic compositions can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

Also disclosed are pharmaceutical packs or kits comprising one or more containers filled with one or more of the ingredients, e.g., compound, carrier suitable for administration.

The disclosed compositions can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In some forms, microparticles containing the disclosed proteins or nucleic acid molecules can be formulated for parenteral administration. The preparation of an aqueous composition that contains one or more agents, such as a protein or nucleic acid molecule as disclosed, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions can be prepared by incorporating the active ingredients in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

In addition, the disclosed nucleic acid molecules and compositions can be delivered in vivo into a host cell by methods known in the art. In some forms, the disclosed nucleic acid molecules and compositions can be introduced in vivo via a viral vector such as adeno-associated virus (AAV), herpes simplex virus (HSV), retrovirus, papillomavirus, adenovirus, and Epstein-Barr virus (EBV). In addition, the disclosed nucleic acid molecules and compositions can also be introduced in vivo via lipofection (DNA transfection via liposomes prepared from synthetic cationic lipids) (Feigner et al., 1987). Synthetic cationic lipids (LIPOFECTIN, Invitrogen Corp., La Jolla, Calif.) can be used to prepare liposomes to encapsulate the disclosed nucleic acid molecules. The disclosed nucleic acid molecules of the can also be introduced in vivo as naked DNA using methods known in the art, such as transfection, microinjection, electroporation, calcium phosphate precipitation, and by biolistic methods.

D. Methods of Use

Also disclosed are methods for reducing the risk of or treating coronavirus infection. Advantageously, the disclosed methods can induce antigen-specific humoral and cell-mediated immunity. In some forms, the method comprises administering, to a subject in need of such treatment, an effective amount of a fusion protein or fusion nucleic acid molecule as disclosed.

In some forms, the disclosed methods can induce protective immunity against coronavirus infection. In some forms, the method comprises administering a composition comprising a fusion nucleic acid molecule, where the fusion nucleic acid molecule comprises a nucleic acid encoding a coronavirus antigen and a sPD-1 nucleic acid encoding a wild-type soluble PD1 protein, a nucleic acid encoding a spd1-14 del protein, or a nucleic acid encoding a spd1-322 del protein. Optionally, a nucleic acid encoding Fc domain and a linker nucleic acid sequence that links the sPD-1 nucleic acid and the antigen nucleic acid can be included. In some forms, the composition is administered by intramuscular injection via electroporation (EP).

In some forms, the method comprises administering a composition comprising a fusion protein, wherein the fusion protein comprises a coronavirus antigen and a soluble PD-1 protein selected from a wild-type soluble PD1 protein, a spd1-14del protein, or a spd1-322 del protein. Optionally, a Fc domain and a linker sequence that links the sPD-1 protein and the antigen protein can be included.

The methods can be used for prevention and/or treatment of coronavirus infection.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof. Prevention, as used herein, does not require complete inhibition or elimination of symptoms.

The term "subject," as used herein, describes an organism, including mammals such as primates, to which treatment with the disclosed compositions can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

In some forms, in case of prevention of coronavirus infection, the sPD-1-based composition can be administered to a subject that does not suffer from the coronavirus infection to be prevented or a subject that does not exhibit symptoms of the coronavirus infection to be prevented.

In some forms, the disclosed methods can be used in the prevention and/or treatment of infection by COVID-19, SARS, or MERS.

The disclosed compositions and vaccines can be used to effectively increase viral titer or elicit an immune response in a subject in need thereof. In some aspects, subjects can include the elderly (e.g., >65 years old), young children (e.g., <5 years old). Methods for improving immune response in children using adjuvanted formulations are disclosed for example in U.S. Publication 2017/0202955.

The disclosed compositions and vaccines can generally be administered directly to a mammal in need thereof to increase viral titer in the mammal and elicit an immune response.

Typically the composition is administered in an effective amount to induce an immune response against a one or more coronavirus antigens. For example, an effective amount of the composition generally results in production of antibody and/or activated T cells that kill or limit proliferation of or infection by the coronavirus.

The composition can typically be used to elicit systemic and/or mucosal immunity, for example to elicit an enhanced systemic and/or mucosal immunity. For example, the immune response can be characterized by the induction of a serum IgG and/or intestinal IgA immune response. Typically, the level of protection against influenza infection can be more than 50%, e.g., 60%, 70%, 80%, 90%, 91%, 92%, 93%, 94%, 95%, 96%, 97%, 98%, 99%, or more. In one aspect, the level of protection can be 100%.

The immune response induced by the disclosed compositions and methods can be one or both of a TH1 immune response and a TH2 response. The immune response can be an improved or an enhanced or an altered immune response. The immune response can be one or both of a systemic and a mucosal immune response. For example, the immune response can be an enhanced systemic and/or mucosal response. An enhanced systemic and/or mucosal immunity is reflected in an enhanced TH1 and/or TH2 immune response. For example, the enhanced immune response can include an increase in the production of IgG1 and/or IgG2a and/or IgA. In another aspect the mucosal immune response can be a TH2 immune response. For example, the mucosal immune response can include an increase in the production of IgA.

Typically, activated TH2 cells enhance antibody production and are therefore of value in responding to extracellular infections. Activated TH2 cells can typically secrete one or more of IL-4, IL-5, IL-6, and IL-10. A TH2 immune response can also result in the production of IgG1, IgE, IgA, and/or memory B cells for future protection. In general, a TH2 immune response can include one or more of an increase in one or more of the cytokines associated with a TH2 immune response (such as IL-4, IL-5, IL-6 and IL-10), or an increase in the production of IgG1, IgE, IgA and memory B cells. For example, an enhanced TH2 immune response can include an increase in IgG1 production. A TH1 immune response can include one or more of an increase in CTLs, an increase in one or more of the cytokines associated with a TH1 immune response (such as IL-2, IFN-gamma, and TNF-alpha), an increase in activated macrophages, an increase in NK activity, or an increase in the production of IgG2a. For example, the enhanced TH1 immune response can include an increase in IgG2a production.

The disclosed fusion proteins and fusion nucleic acid molecules can be used either alone or in combination with other agents optionally with an immunoregulatory agent capable of eliciting a Th1 and/or Th2 response.

The precise dosage will vary according to a variety of factors such as subject-dependent variables (e.g., age, immune system health, etc.), and age of the subject being treated. Appropriate dosages can be determined by a person skilled in the art, considering the therapeutic context, age, and general health of the recipient. The selected dosage depends upon the desired therapeutic effect, on the route of administration, and on the duration of the treatment desired.

The vaccine composition can be administered in a single dose or a multi-dose format. Vaccines can be prepared with adjuvant hours or days prior to administrations, subject to identification of stabilizing buffer(s) and suitable adjuvant composition. Typically, the dose will be 100 μl administered locally in multiple doses, while systemic or regional administration via subcutaneous, intramuscular, intra-organ, intravenous or intranasal administration can be from for example, 10 to 100 μl.

E. Kits

A kit including the disclosed fusion proteins and/or fusion nucleic acid molecules are also provided. The kit can include a separate container containing a suitable carrier, diluent or excipient. Additionally, the kit can include instructions for mixing or combining ingredients and/or administration.

Compositions can be in liquid form or can be lyophilized. Suitable containers for the compositions include, for example, bottles, vials, syringes, and test tubes. Containers can be formed from a variety of materials, including glass or plastic. A container can have a sterile access port (for example, the container can be an intravenous solution bag or a vial having a stopper pierceable by a hypodermic injection needle).

The kit can further include a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device(s). The kit can further include a third component comprising an adjuvant.

The kit can also include a package insert containing written instructions for methods of inducing immunity, preventing infections, or for treating infections. The package insert can be an unapproved draft package insert or can be a package insert approved by the Food and Drug Administration (FDA) or other regulatory body.

Also disclosed are delivery devices pre-filled with the disclosed compositions.

The compositions are generally formulated as sterile, substantially isotonic and in full compliance with all Good Manufacturing Practice (GMP) regulations of the U.S. Food and Drug Administration.

The disclosed compositions and methods can be further understood through the following numbered paragraphs.

1. A soluble PD-1 fusion protein, comprising a soluble PD-1 protein fragment and an antigenic protein fragment, wherein the soluble PD-1 protein fragment comprises an amino acid sequence selected from the group consisting of SEQ ID NO:1, SEQ ID NO:7, SEQ ID NO:3, SEQ ID NO:5, and SEQ ID NO:9, and wherein the antigenic protein fragment comprises a coronavirus protein fragment.

2. The soluble PD-1 fusion protein of paragraph 1, wherein the coronavirus protein fragment is derived from a coronavirus receptor binding domain (RBD) or a coronavirus nucleoprotein (N).

3. The PD-1 fusion protein of paragraph 1 or 2, wherein the coronavirus protein fragment is derived from a COVID-19, a SARS, or a MERS.

4. The PD-1 fusion protein of any one of paragraphs 1-3, wherein the coronavirus protein fragment is derived from a COVID-19 receptor binding domain (RBD) or a COVID-19 nucleoprotein (N).

5. The PD-1 fusion protein of any one of paragraphs 1-4, further comprising a Fc domain.

6. The PD-1 fusion protein of any one of paragraphs 1-5, further comprising a linker sequence, wherein the linker sequence links the soluble PD-1 protein fragment and the antigenic protein fragment.

7. The PD-1 fusion protein of any one of paragraphs 1-6, comprising both an amino acid sequence selected from the group consisting of SEQ ID NO:1, SEQ ID NO:7, SEQ ID NO:3, SEQ ID NO:5, and SEQ ID NO:9 and an amino acid sequence selected from the group consisting of SEQ ID NO:11 or SEQ ID NO:12.

8. A sPD-1 fusion nucleic acid molecule encoding a PD-1 fusion protein of any one of paragraphs 1-7.

9. The sPD-1 fusion nucleic acid molecule of paragraph 8, wherein the nucleic acid molecule comprises both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

10. A vaccine composition comprising the sPD-1 fusion nucleic acid molecule of paragraph 8 or 9.

11. A method for treating a subject at risk of or suffering a coronavirus infection, comprising administering to the subject an effective amount of the sPD-1 fusion nucleic acid of paragraph 8 or 9 or of the vaccine composition of paragraph 10.

12. The method of paragraph 11, wherein the coronavirus infection is of COVID-19, SARS, or MERS.

13. The method of paragraph 11 or 12, wherein the sPD-1 fusion nucleic acid comprises a nucleic acid fragment encoding the coronavirus protein fragment, wherein the coronavirus protein fragment is derived from a COVID-19 receptor binding domain (RBD) or a COVID-19 nucleoprotein (N), and wherein the coronavirus infection is of COVID-19.

14. The method of any one of paragraphs 11-13, wherein the sPD-1 fusion nucleic acid comprises both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

15. The method of any one of paragraphs 11-14, wherein the sPD-1 fusion nucleic acid is administered by injection.

16. The method of any one of paragraphs 11-14, wherein the sPD-1 fusion nucleic acid is administered via electroporation.

17. A method for treating a subject at risk of or suffering a coronavirus infection, comprising administering to the subject an effective amount of a fusion protein of any one of paragraphs 1-7.

18. The method of paragraph 17, wherein the coronavirus infection is of COVID-19, SARS, or MERS.

19. The method of paragraph 17 or 18, wherein the coronavirus protein fragment is derived from a COVID-19 receptor binding domain (RBD) or a COVID-19 nucleoprotein (N).

20. The method of any one of paragraphs 11-19, wherein the subject is at risk of a coronavirus infection.

21. The method of any one of paragraphs 11-19, wherein the subject is suffering from a coronavirus infection.

It is understood that the disclosed methods and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, reference to "an antigen" includes a plurality of such antigens, reference to "the antigen" is a reference to one or more aptamers and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e., a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present methods and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different moieties does not indicate that the listed moieties are obvious one to the other, nor is it an admission of equivalence or obviousness.

We claim:

1. A soluble PD-1 fusion protein, comprising a soluble PD-1 protein fragment and an antigenic protein fragment, wherein the soluble PD-1 protein fragment comprises an amino acid sequence selected from the group consisting of SEQ ID NO:1, SEQ ID NO:7, SEQ ID NO:3, SEQ ID NO:5, and SEQ ID NO:9, and wherein the antigenic protein fragment comprises a fragment of a COVID-19 receptor binding domain (RBD) or a COVID-19 nucleoprotein (N).

2. The PD-1 fusion protein of claim 1, further comprising a Fc domain.

3. The PD-1 fusion protein of claim 1, further comprising a linker sequence, wherein the linker sequence links the soluble PD-1 protein fragment and the antigenic protein fragment.

4. The PD-1 fusion protein of claim 1, comprising both an amino acid sequence selected from the group consisting of SEQ ID NO:1, SEQ ID NO:7, SEQ ID NO:3, SEQ ID NO:5, and SEQ ID NO:9 and an amino acid sequence selected from the group consisting of SEQ ID NO:11 or SEQ ID NO:12.

5. A sPD-1 fusion nucleic acid molecule encoding a PD-1 fusion protein of claim 1.

6. The sPD-1 fusion nucleic acid molecule of claim 5, wherein the nucleic acid molecule comprises both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

7. A vaccine composition comprising the sPD-1 fusion nucleic acid molecule of claim 5.

8. A method for treating a subject at risk of or suffering a COVID-19 infection, comprising administering to the subject an effective amount of the sPD-1 fusion nucleic acid of claim 5.

9. The method of claim 8, wherein the sPD-1 fusion nucleic acid comprises both a nucleic acid sequence selected from the group consisting of SEQ ID NO:4, SEQ ID NO:6, and SEQ ID NO:10, and a nucleic acid sequence encoding an amino acid sequence selected from the group consisting of SEQ ID NO:11 or SEQ ID NO:12.

10. The method of claim 8, wherein the sPD-1 fusion nucleic acid is administered by injection.

11. The method of claim 8, wherein the sPD-1 fusion nucleic acid is administered via electroporation.

12. A method for treating a subject at risk of or suffering a COVID-19 infection, comprising administering to the subject an effective amount of a fusion protein of claim 1.

13. The method of claim 8, wherein the subject is at risk of a COVID-19 infection.

14. The method of claim 8, wherein the subject is suffering from a COVID-19 infection.

* * * * *

SEQUENCE LISTING

<160> NUMBER OF SEQ ID NOS: 26

<210> SEQ ID NO 1
<211> LENGTH: 178
<212> TYPE: PRT
<213> ORGANISM: Mus musculus
<220> FEATURE:
<221> NAME/KEY: DOMAIN
<222> LOCATION: (1)..(178)
<223> OTHER INFORMATION: wild-type soluble extracellular domain of mouse
      PD-1 (mouse spd1)

<400> SEQUENCE: 1

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Gly Phe Arg Gly Gly Ser Gly
                165                 170                 175

Gly Gly
```

<210> SEQ ID NO 2
<211> LENGTH: 537
<212> TYPE: DNA
<213> ORGANISM: Mus musculus
<220> FEATURE:
<221> NAME/KEY: misc_feature
<222> LOCATION: (1)..(537)
<223> OTHER INFORMATION: wild-type soluble extracellular domain of mouse
      PD-1 (mouse spd1)

<400> SEQUENCE: 2

```
atgtgggtcc ggcaggtacc ctggtcattc acttgggctg tgctgcagtt gagctggcaa      60
tcagggtggc ttctagaggt ccccaatggg ccctggaggt ccctcacctt ctacccagcc     120
tggctcacag tgtcagaggg agcaaatgcc accttcacct gcagcttgtc caactggtcg     180
gaggatctta tgctgaactg gaaccgcctg agtcccagca accagactga aaaacaggcc     240
gccttctgta tggtttgag ccaacccgtc caggatgccc gcttccagat catacagctg     300
cccaacaggc atgacttcca catgaacatc cttgacacac ggcgcaatga cagtggcatc     360
tacctctgtg ggccatctc cctgcacccc aaggcaaaaa tcgaggagag ccctggagca     420
gagctcgtgg taacagagag aatcctggag acctcaacaa gatatcccag ccctcgccc     480
```

```
aaaccagaag gccggtttca accggaattc cggggtggtg gtggttcagg aggagga      537
```

<210> SEQ ID NO 3
<211> LENGTH: 164
<212> TYPE: PRT
<213> ORGANISM: Artificial Sequence
<220> FEATURE:
<223> OTHER INFORMATION: amino acid sequence of mspd1-14del

<400> SEQUENCE: 3

```
Met Trp Val Arg Gln Val Pro Trp Ser Phe Thr Trp Ala Val Leu Gln
1               5                   10                  15

Leu Ser Trp Gln Ser Gly Trp Leu Leu Ala Trp Leu Thr Val Ser Glu
            20                  25                  30

Gly Ala Asn Ala Thr Phe Thr Cys Ser Leu Ser Asn Trp Ser Glu Asp
        35                  40                  45

Leu Met Leu Asn Trp Asn Arg Leu Ser Pro Ser Asn Gln Thr Glu Lys
    50                  55                  60

Gln Ala Ala Phe Cys Asn Gly Leu Ser Gln Pro Val Gln Asp Ala Arg
65                  70                  75                  80

Phe Gln Ile Ile Gln Leu Pro Asn Arg His Asp Phe His Met Asn Ile
                85                  90                  95

Leu Asp Thr Arg Arg Asn Asp Ser Gly Ile Tyr Leu Cys Gly Ala Ile
            100                 105                 110

Ser Leu His Pro Lys Ala Lys Ile Glu Glu Ser Pro Gly Ala Glu Leu
        115                 120                 125

Val Val Thr Glu Arg Ile Leu Glu Thr Ser Thr Arg Tyr Pro Ser Pro
    130                 135                 140

Ser Pro Lys Pro Glu Gly Arg Phe Gln Pro Glu Phe Arg Gly Gly Gly
145                 150                 155                 160

Ser Gly Gly Gly
```

<210> SEQ ID NO 4
<211> LENGTH: 495
<212> TYPE: DNA
<213> ORGANISM: Artificial Sequence
<220> FEATURE:
<223> OTHER INFORMATION: nucleic acid sequence of mspd1-14del DNA

<400> SEQUENCE: 4

```
atgtgggtcc ggcaggtacc ctggtcattc acttgggctg tgctgcagtt gagctggcaa      60
tcagggtggc ttctagcctg gctcacagtg tcagagggag caaatgccac cttcacctgc     120
agcttgtcca actggtcgga ggatcttatg ctgaactgga accgcctgag tcccagcaac     180
cagactgaaa aacaggccgc cttctgtaat ggtttgagcc aacccgtcca ggatgcccgc     240
ttccagatca tacagctgcc caacaggcat gacttccaca tgaacatcct tgacacacgg     300
cgcaatgaca gtggcatcta cctctgtggg gccatctccc tgcacccaa ggcaaaaatc      360 gaggagagcc ctggagcaga gctcgtggta acagagagaa tcctggagac ctcaacaaga     420
tatcccagcc cctcgcccaa accagaaggc cggtttcaac cggaattccg ggtggtggt      480 ggttcaggag gagga                                                      495
```

<210> SEQ ID NO 5
<211> LENGTH: 178
<212> TYPE: PRT
<213> ORGANISM: Artificial Sequence
<220> FEATURE:
<223> OTHER INFORMATION: amino acid sequence of mspd1-322mu

<400> SEQUENCE: 5

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Val Asn Ile Leu Asp
                100                 105                 110

Thr Arg Arg Asn Asp Ser Gly Ile Tyr Leu Cys Gly Ala Ile Ser Leu
            115                 120                 125

His Pro Lys Ala Lys Ile Glu Glu Ser Pro Gly Ala Glu Leu Val Val
130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Glu Phe Arg Gly Gly Gly Ser Gly
                165                 170                 175

Gly Gly

<210> SEQ ID NO 6
<211> LENGTH: 537
<212> TYPE: DNA
<213> ORGANISM: Artificial Sequence
<220> FEATURE:
<223> OTHER INFORMATION: nucleic acid sequence of mspd1-322mu DNA

<400> SEQUENCE: 6
atgtgggtcc ggcaggtacc ctggtcattc acttgggctg tgctgcagtt gagctggcaa        60
tcagggtggc ttctagaggt ccccaatggg ccctggaggt ccctcacctt ctacccagcc       120
tggctcacag tgtcagaggg agcaaatgcc accttcacct gcagcttgtc caactggtcg       180
gaggatctta tgctgaactg gaaccgcctg agtcccagca accagactga aaacaggcc        240
gccttctgta tggtttgag ccaacccgtc caggatgccc gcttccagat catacagctg        300
cccaacaggc atgacttcca cgtgaacatc cttgacacac ggcgcaatga cagtggcatc       360
tacctctgtg gggccatctc cctgcacccc aaggcaaaaa tcgaggagag ccctggagca       420
gagctcgtgg taacagagag aatcctggag acctcaacaa gatatcccag cccctcgccc       480
aaaccagaag gccggtttca accggaattc cggggtggtg gtggttcagg aggagga        537

<210> SEQ ID NO 7
<211> LENGTH: 176
<212> TYPE: PRT
<213> ORGANISM: Homo sapiens
<220> FEATURE:
<221> NAME/KEY: DOMAIN
<222> LOCATION: (1)..(176)
<223> OTHER INFORMATION: wild-type soluble extracellular domain of human
      PD-1 (hhuman spd1)

<400> SEQUENCE: 7

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Pro Glu Phe Arg Gly Gly Gly Ser Gly Gly Gly
                165                 170                 175

<210> SEQ ID NO 8
<211> LENGTH: 531
<212> TYPE: DNA
<213> ORGANISM: Homo sapiens
<220> FEATURE:
<221> NAME/KEY: misc_feature
<222> LOCATION: (1)..(531)
<223> OTHER INFORMATION: wild-type soluble extracellular domain of human
      PD-1 (human spd1)

<400> SEQUENCE: 8
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aagacgcaga tcaaagagag cctgcgggca     420
gagctcaggg tgacagagag aagggcagaa gtgcccacag cccacccag ccctcacccc      480 aggccagccg gccagccgga attccggggt ggtggtggtt caggaggagg a              531

<210> SEQ ID NO 9
<211> LENGTH: 162
<212> TYPE: PRT
<213> ORGANISM: Artificial Sequence
<220> FEATURE:
<223> OTHER INFORMATION: amino acid sequence of hspd1-14del

<400> SEQUENCE: 9

Met Gln Ile Pro Gln Ala Pro Trp Pro Val Trp Ala Val Leu Gln
1               5                   10                  15

Leu Gly Trp Arg Pro Gly Trp Phe Leu Ala Leu Leu Val Val Thr Glu
                20                  25                  30

```
Gly Asp Asn Ala Thr Phe Thr Cys Ser Phe Ser Asn Thr Ser Glu Ser
            35                  40                  45

Phe Val Leu Asn Trp Tyr Arg Met Ser Pro Ser Asn Gln Thr Asp Lys
 50                  55                  60

Leu Ala Ala Phe Pro Glu Asp Arg Ser Gln Pro Gly Asp Cys Arg
 65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
                100                 105                 110

Ser Leu Ala Pro Lys Ala Gln Ile Lys Glu Ser Leu Arg Ala Glu Leu
                115                 120                 125

Arg Val Thr Glu Arg Arg Ala Glu Val Pro Thr Ala His Pro Ser Pro
            130                 135                 140

Ser Pro Arg Pro Ala Gly Gln Pro Glu Phe Arg Gly Gly Ser Gly
145                 150                 155                 160

Gly Gly
```

<210> SEQ ID NO 10
<211> LENGTH: 486
<212> TYPE: DNA
<213> ORGANISM: Artificial Sequence
<220> FEATURE:
<223> OTHER INFORMATION: nucleic acid sequence of hspd1-14del DNA

<400> SEQUENCE: 10

```
atgcagatcc cacaggcgcc ctggccagtc gtctgggcgg tgctacaact gggctggcgg    60
ccaggatggt tcttagccct gctcgtggtg accgaagggg acaacgccac cttcacctgc   120
agcttctcca acacatcgga gagcttcgtg ctaaactggt accgcatgag ccccagcaac   180
cagacggaca agctggccgc cttccccgag gaccgcagcc agcccggcca ggactgccgc   240
ttccgtgtca cacaactgcc caacgggcgt gacttccaca tgagcgtggt cagggcccgg   300
cgcaatgaca gcggcaccta cctctgtggg gccatctccc tggcccccaa gacgcagatc   360
aaagagagcc tgcgggcaga gctcagggtg acagagagaa gggcagaagt gcccacagcc   420
caccccagcc cctcacccag gccagccggc cagccggaat tccggggtgg tggtggttca   480
ggagga                                                              486
```

<210> SEQ ID NO 11
<211> LENGTH: 238
<212> TYPE: PRT
<213> ORGANISM: Unknown
<220> FEATURE:
<223> OTHER INFORMATION: COVID-19 RBD protein

<400> SEQUENCE: 11

```
Phe Thr Val Glu Lys Gly Ile Tyr Gln Thr Ser Asn Phe Arg Val Gln
 1               5                  10                  15

Pro Thr Glu Ser Ile Val Arg Phe Pro Asn Ile Thr Asn Leu Cys Pro
                20                  25                  30

Phe Gly Glu Val Phe Asn Ala Thr Arg Phe Ala Ser Val Tyr Ala Trp
            35                  40                  45

Asn Arg Lys Arg Ile Ser Asn Cys Val Ala Asp Tyr Ser Val Leu Tyr
 50                  55                  60

Asn Ser Ala Ser Phe Ser Thr Phe Lys Cys Tyr Gly Val Ser Pro Thr
 65                  70                  75                  80
```

```
Lys Leu Asn Asp Leu Cys Phe Thr Asn Val Tyr Ala Asp Ser Phe Val
                85                  90                  95

Ile Arg Gly Asp Glu Val Arg Gln Ile Ala Pro Gly Gln Thr Gly Lys
            100                 105                 110

Ile Ala Asp Tyr Asn Tyr Lys Leu Pro Asp Asp Phe Thr Gly Cys Val
        115                 120                 125

Ile Ala Trp Asn Ser Asn Asn Leu Asp Ser Lys Val Gly Gly Asn Tyr
    130                 135                 140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
            180                 185                 190

Gln Pro Thr Asn Gly Val Gly Tyr Gln Pro Tyr Arg Val Val Val Leu
        195                 200                 205

Ser Phe Glu Leu Leu His Ala Pro Ala Thr Val Cys Gly Pro Lys Lys
    210                 215                 220

Ser Thr Asn Leu Val Lys Asn Lys Cys Val Asn Phe Asn Phe
225                 230                 235

<210> SEQ ID NO 12
<211> LENGTH: 419
<212> TYPE: PRT
<213> ORGANISM: Unknown
<220> FEATURE:
<223> OTHER INFORMATION: COVID-19 N protein

<400> SEQUENCE: 12

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205
```

-continued

```
Arg Met Ala Gly Asn Gly Gly Asp Ala Ala Leu Ala Leu Leu Leu Leu
        210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Ala Asp Glu Thr Gln Ala Leu Pro Gln
370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 13
<211> LENGTH: 288
<212> TYPE: PRT
<213> ORGANISM: Oryctolagus cuniculus
<220> FEATURE:
<221> NAME/KEY: DOMAIN
<222> LOCATION: (1)..(288)
<223> OTHER INFORMATION: amino acid sequence of rabbit Fc domain

<400> SEQUENCE: 13

Met Gln Tyr Ile Lys Ala Asn Ser Lys Phe Ile Gly Ile Thr Glu Leu
1               5                   10                  15

Lys Lys Leu Gly Gly Ser Asn Asp Ile Phe Asn Asn Phe Thr Val Ser
            20                  25                  30

Phe Trp Leu Arg Val Pro Lys Val Ser Ala Ser His Leu Glu Gln Tyr
        35                  40                  45

Leu Glu Ala Thr Asn Thr Lys Val Asp Lys Thr Val Ala Pro Ser Thr
    50                  55                  60

Cys Ser Lys Pro Met Cys Pro Pro Glu Leu Leu Gly Gly Pro Ser
65                  70                  75                  80

Val Phe Ile Phe Pro Pro Lys Pro Lys Asp Thr Leu Met Ile Ser Arg
                85                  90                  95

Thr Pro Glu Val Thr Cys Val Val Asp Val Ser Gln Asp Asp Pro
            100                 105                 110

Glu Val Gln Phe Thr Trp Tyr Ile Asn Asn Glu Gln Val Arg Thr Ala
        115                 120                 125

Arg Pro Pro Leu Arg Glu Gln Gln Phe Asn Ser Thr Ile Arg Val Val
```

```
                130                 135                 140
Ser Thr Leu Pro Ile Ala His Gln Asp Trp Leu Arg Gly Lys Glu Phe
145                 150                 155                 160

Lys Cys Lys Val His Asn Lys Ala Leu Pro Ala Pro Ile Glu Lys Thr
                165                 170                 175

Ile Ser Lys Ala Arg Gly Gln Pro Leu Glu Pro Lys Val Tyr Thr Met
                180                 185                 190

Gly Pro Pro Arg Glu Glu Leu Ser Ser Arg Ser Val Ser Leu Thr Cys
            195                 200                 205

Met Ile Asn Gly Phe Tyr Pro Ser Asp Ile Ser Val Glu Trp Glu Lys
            210                 215                 220

Asn Gly Lys Ala Glu Asp Asn Tyr Lys Thr Thr Pro Thr Val Leu Asp
225                 230                 235                 240

Ser Asp Gly Ser Tyr Phe Leu Tyr Ser Lys Leu Ser Val Pro Thr Ser
                245                 250                 255

Glu Trp Gln Arg Gly Asp Val Phe Thr Cys Ser Val Met His Glu Ala
                260                 265                 270

Leu His Asn His Tyr Thr Gln Lys Ser Ile Ser His Ser Pro Gly Lys
            275                 280                 285
```

<210> SEQ ID NO 14
<211> LENGTH: 820
<212> TYPE: DNA
<213> ORGANISM: Oryctolagus cuniculus
<220> FEATURE:
<221> NAME/KEY: misc_feature
<222> LOCATION: (1)..(820)
<223> OTHER INFORMATION: nucleic acid sequence of rabbit Fc DNA

<400> SEQUENCE: 14

```
ctgggaggct caaacgacat attcaacaac ttcacagtgt ccttctggtt gcgggttccc    60
aaggtctctg ctagccacct cgaacaatac ctggaggcca ccaacaccaa agtggacaag   120
accgttgcgc cctcgacatg cagcaagccc atgtgcccac cccctgaact cctgggggga   180
ccgtctgtct tcatcttccc cccaaaaccc aaggacaccc tcatgatctc acgcaccccc   240
gaggtcacat gcgtggtggt ggacgtgagc caggatgacc ccgaggtgca gttcacatgg   300
tacataaaca acgagcaggt gcgcaccgcc cggccgccgc tacgggagca gcagttcaac   360
agcacgatcc gcgtggtcag caccctcccc atcgcgcacc aggactggct gaggggcaag   420
gagttcaagt gcaaagtcca acaaggca ctcccggccc ccatcgagaa aaccatctcc     480
aaagccagag ggcagcccct ggagccgaag gtctacacca tgggcccctcc ccggaggag   540
```

```
Gly Gly Gly Ser Gly Gly Gly
1               5

<210> SEQ ID NO 16
<211> LENGTH: 27
<212> TYPE: PRT
<213> ORGANISM: Artificial Sequence
<220> FEATURE:
<223> OTHER INFORMATION: amino acid sequence of a linker sequence

<400> SEQUENCE: 16

Gly Leu Tyr Gly Leu Tyr Gly Leu Tyr Gly Leu Tyr Gly Leu Tyr Gly
1               5                   10                  15

Leu Tyr Gly Leu Tyr Gly Leu Tyr Gly Leu Tyr
            20                  25

<210> SEQ ID NO 17
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 17

Glu Glu Glu Glu Glu Glu Glu Glu Glu
1               5

<210> SEQ ID NO 18
<211> LENGTH: 27
<212> TYPE: PRT
<213> ORGANISM: Artificial Sequence
<220> FEATURE:
<223> OTHER INFORMATION: amino acid sequence of a linker sequence

<400> SEQUENCE: 18

Ser Glu Arg Ser Glu Arg Ser Glu Arg Ser Glu Arg Ser Glu Arg Ser
1               5                   10                  15

Glu Arg Ser Glu Arg Ser Glu Arg Ser Glu Arg
            20                  25

<210> SEQ ID NO 19
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 19

Gly Gly Gly Gly Gly Cys Pro Pro Cys
1               5

<210> SEQ ID NO 20
<211> LENGTH: 21
<212> TYPE: PRT
<213> ORGANISM: Artificial Sequence
<220> FEATURE:
<223> OTHER INFORMATION: amino acid sequence of a linker sequence

<400> SEQUENCE: 20

Gly Leu Tyr Gly Leu Tyr Gly Leu Tyr Gly Leu Tyr Ser Glu Arg Ser
1               5                   10                  15

Glu Arg Ser Glu Arg
            20
```

```
<210> SEQ ID NO 21
<211> LENGTH: 13
<212> TYPE: PRT
<213> ORGANISM: Artificial Sequence
<220> FEATURE:
<223> OTHER INFORMATION: amino acid sequence of a linker sequence

<400> SEQUENCE: 21

Ser Cys Val Pro Leu Met Arg Cys Gly Gly Cys Cys Asn
1               5                   10

<210> SEQ ID NO 22
<211> LENGTH: 14
<212> TYPE: PRT
<213> ORGANISM: Artificial Sequence
<220> FEATURE:
<223> OTHER INFORMATION: amino acid sequence of a linker sequence

<400> SEQUENCE: 22

Pro Ser Cys Val Pro Leu Met Arg Cys Gly Gly Cys Cys Asn
1               5                   10

<210> SEQ ID NO 23
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 23

Gly Asp Leu Ile Tyr Arg Asn Gln Lys
1               5

<210> SEQ ID NO 24
<211> LENGTH: 23
<212> TYPE: PRT
<213> ORGANISM: Artificial Sequence
<220> FEATURE:
<223> OTHER INFORMATION: amino acid sequence of a linker sequence

<400> SEQUENCE: 24

Gly Gly Gly Gly Gly Gly Gly Gly Gly Pro Ser Cys Val Pro Leu Met
1               5                   10                  15

Arg Cys Gly Gly Cys Cys Asn
            20

<210> SEQ ID NO 25
<211> LENGTH: 9
<212> TYPE: PRT
<213> ORGANISM: Artificial Sequence
<220> FEATURE:
<223> OTHER INFORMATION: amino acid sequence of a linker sequence

<400> SEQUENCE: 25

Ala Met Gln Met Leu Lys Asp Thr Ile
1               5

<210> SEQ ID NO 26
<211> LENGTH: 20
<212> TYPE: PRT
<213> ORGANISM: Artificial Sequence
<220> FEATURE:
<223> OTHER INFORMATION: amino acid sequence of a linker sequence
```

-continued

<400> SEQUENCE: 26

```
Thr Ser Asn Pro Pro Ile Pro Val Gly Asp Ile Tyr Lys Arg Trp Ile
1               5                   10                  15

Ile Leu Gly Leu
            20
```